(12) United States Patent
Tirtowidjojo et al.

(10) Patent No.: US 8,558,029 B2
(45) Date of Patent: Oct. 15, 2013

(54) PROCESS FOR THE CONTINUOUS PRODUCTION OF HIGH PURITY PHENOLIC GLYCOL ETHER

(75) Inventors: Max Tirtowidjojo, Lake Jackson, TX (US); Edward D. Daugs, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 441 days.

(21) Appl. No.: 12/745,648

(22) PCT Filed: Dec. 8, 2008

(86) PCT No.: PCT/US2008/085822
§ 371 (c)(1),
(2), (4) Date: Sep. 22, 2010

(87) PCT Pub. No.: WO2009/076275
PCT Pub. Date: Jun. 18, 2009

(65) Prior Publication Data
US 2011/0009675 A1    Jan. 13, 2011

Related U.S. Application Data

(60) Provisional application No. 61/013,108, filed on Dec. 12, 2007.

(51) Int. Cl.
*C07C 43/23* (2006.01)
(52) U.S. Cl.
USPC .......................................................... 568/648
(58) Field of Classification Search
USPC ....................................................... 568/648
See application file for complete search history.

(56) References Cited

U.S. PATENT DOCUMENTS

| | | | | |
|---|---|---|---|---|
| 1,976,677 | A | * | 10/1934 | Wittwer .......................... 560/240 |
| 2,815,322 | A | | 12/1957 | Higgins |
| 2,852,566 | A | | 9/1958 | Emil |
| 2,888,489 | A | * | 5/1959 | Horsley et al. ................. 568/609 |
| 3,354,227 | A | | 11/1967 | Ewald |
| 3,364,267 | A | | 1/1968 | Horsley |
| 3,525,773 | A | | 8/1970 | Schulze |
| 3,642,911 | A | | 2/1972 | Schulze |
| 3,644,534 | A | | 2/1972 | Reabe et al. |
| 3,935,279 | A | | 1/1976 | Cocuzza et al. |
| 2004/0181099 | A1 | | 9/2004 | Hirano et al. |

FOREIGN PATENT DOCUMENTS

DE    1096366    1/1961

* cited by examiner

*Primary Examiner* — Rosalynd Keys
(74) *Attorney, Agent, or Firm* — Whyte Hirschboeck Dudek S.C.

(57) ABSTRACT

Phenolic glycol ethers, e.g., ethylene glycol phenyl ether, are prepared by a continuous, nonaqueous process comprising the steps of (A) contacting under isothermal reactive conditions in a first reactor or reaction zone an alkylene oxide, e.g., ethylene oxide, with (i) a stoichiometric molar excess of a phenolic compound, e.g., phenol, and (ii) a catalytic amount of a base, e.g., sodium hydroxide, homogeneously dispersed throughout the phenolic compound, to form a first intermediate phenolic glycol ether product, (Bj transferring the first intermediate phenolic glycol ether product to a second reactor or reaction zone, and (C) subjecting the first intermediate phenolic glycol ether product to adiabatic reactive conditions in the second reactor or reaction zone to form a second intermediate phenolic glycol ether product comprising phenolic glycol ether, unreacted phenolic compound, catalyst, water and byproduct glycols. In addition, the mono-/di-product weight ratio can be adjusted by increasing or decreasing the amount of base catalyst employed.

9 Claims, 9 Drawing Sheets

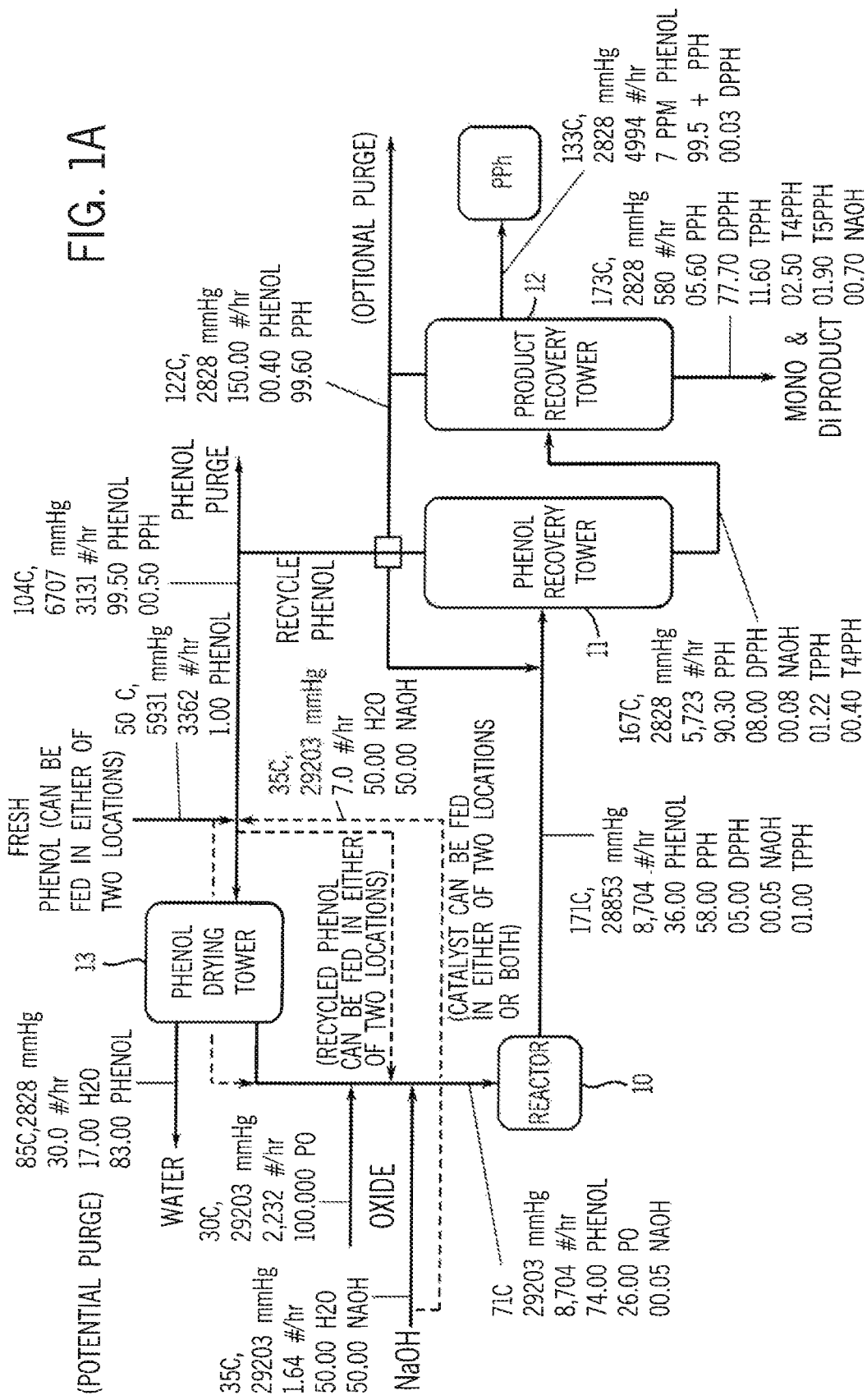

PROCESS FOR THE CONTINUOUS PRODUCTION OF HIGH PURITY PHENOLIC GLYCOL ETHER

CROSS-REFERENCE TO RELATED APPLICATIONS

This application claims the benefit of U.S. Provisional Application No. 61/013,108, filed Dec. 12, 2007, which application is fully incorporated herein by reference.

FIELD OF THE INVENTION

This invention relates to phenolic glycol ethers. In one aspect, the invention relates to a continuous process for the manufacture of phenolic glycol ether while in another aspect, the invention relates to such a continuous process using a base catalyst homogeneously dispersed in an excess of a phenolic compound. In yet another aspect, the invention relates to a continuous process for the manufacture of phenolic glycol ether using a combination of isothermal and adiabatic reactors or reactor zones. In still another aspect, the invention relates to a process of adjusting the mono-/di-phenolic glycol ether weight ratio by adjusting the catalyst concentration.

BACKGROUND OF THE INVENTION

The manufacture of phenolic glycol ethers (also know as alkylene phenolic glycol ethers), e.g., propylene glycol phenyl ether (PPh) and/or ethylene glycol phenyl ether (EPh), is long known and practiced. U.S. Pat. No. 2,852,566 teaches a semi-batch process that uses an ion-exchange resin as a heterogeneous catalyst containing quaternary ammonium hydroxide groups, U.S. Pat. No. 3,642,911 describes a batch reaction system for preparing phenoxyethanol using excess ethylene oxide in presence of urea as catalyst. U.S. Pat. No. 3,525,773 describes a process similar to that of U.S. Pat. No. 3,642,911 except that its process uses ammonia or an amide as the catalyst. Other similar teachings include U.S. Pat. Nos. 3,644,534, 3,364,267 and 3,354,227 and U.S. 2004/0181099.

One common process for making phenolic glycol ether, e.g., PPh and/or EPh, is a batch process in which propylene oxide (PO) and/or ethylene oxide (EO) is reacted with phenol in the presence of sodium hydroxide (NaOH) which serves as a catalyst. The oxides are added continuously into a mixture of phenol and NaOH catalyst until the amount of residual phenol in the reactor effluent is less than 100 parts per million (ppm). In order to achieve low oxide (less than (<) 15 ppm EO and <400 ppm PO) concentration in the reactor effluent, a long residence time (e.g., greater than 10 hours) is necessary to complete the oxide conversion and this, in turn, imparts a low capacity (i.e., a poor production rate) to the process. Moreover, the long residence time and the oxide to phenol weight ratio of slightly (e.g., 5% excess oxide) greater than 1 employed to minimize unreacted phenol and oxide is such that a significant amount of higher homolog products, e.g., dipropylene glycol phenyl ether, and other impurities are produced. This, in turn, requires significant distillation effort to purify the EPh and PPh even if the reactor effluent is neutralized with an acid, e.g., phosphoric acid, to remove the NaOH catalyst in order to avoid, further reaction. In addition, filtration of the resulting salt, i.e., sodium phosphate, requires an intensive operation.

In those instances in which a significant amount of higher homolog is desired, e.g., diethylene or triethylene glycol phenyl ether, conventional practice is to recycle mono-product to react further with the oxides to produce the desired higher homolog products (in particular the di-product). However this lowers the productivity of the process as a larger reactor volume is needed to accommodate the longer reaction time, or it requires a larger capital investment so as to allow recycling of mono-products. Moreover, while a simple phenol drying unit may be sufficient for mono-product production, usually a more intense operation, e.g., two or more phenol drying units coupled in series, is necessary to remove water from phenol recycle in order to obtain the desired purity in glycol formation.

Accordingly, of interest to the manufacturers of EPh and PPh is an alternative process, ideally a continuous process, that will eliminate the need for catalyst neutralization, salt filtration, and the long residence time while at the same time improving the selectivity, and hence quality, of the product. Also of interest is the ability to affect the mono-/di-product ratio without having to recycle mono-product.

SUMMARY OF THE INVENTION

In one embodiment, the invention is the continuous production of phenolic glycol ether by a process comprising the steps of (A) contacting under isothermal reactive conditions in a first reactor or reaction zone an alkylene oxide, e.g., ethylene or propylene oxide, with (i) a stoichiometric molar excess of a phenolic compound, e.g., phenol, and (ii) a catalytic amount of a base, e.g., sodium or potassium hydroxide, homogeneously dispersed throughout the phenolic compound, to form a first intermediate phenolic glycol ether product, (B) transferring the first intermediate phenolic glycol ether product to a second reactor or reaction zone, and (C) subjecting the first intermediate phenolic glycol ether product to adiabatic reactive conditions in the second reactor or reaction zone to form a second intermediate phenolic glycol ether product comprising phenolic glycol ether, unreacted phenolic compound, catalyst, water and byproduct glycols. Within the first reactor or reaction zone operated under isothermal reactive conditions, a majority of the oxide is converted to the first intermediate phenolic glycol ether product. Within the second reactor or reaction zone operated under adiabatic reactive conditions, the remainder of the oxide is converted to form the second intermediate phenolic glycol ether product. Other than the small amount of water used to dissolve the catalyst or that introduced as an impurity or generated as a byproduct, the process is nonaqueous.

In one embodiment, the inventive process further comprises the step of (D) transferring the second intermediate phenolic glycol ether product from the second reactor or reaction zone to a separation station or zone, e.g., a distillation column, at which unreacted phenolic compound and water are separated and recovered from the second intermediate phenolic glycol ether product to form a recovered phenolic stream comprising unreacted phenolic compound and water.

In one embodiment, the inventive process further comprises the step of (E) transferring the recovered phenolic stream to a drying station, e.g., a distillation column operated at a temperature and pressure that allows for the separation of water (the light key or component) from the phenol (the heavy key or component). At this station, water is removed from the recovered phenolic stream to form a recycle phenolic stream comprising unreacted phenolic compound and catalyst. While not all of the water is removed at this step, enough of the water is removed to prevent water accumulation and this, in turn, reduces the production of glycols which are impurities in the phenolic glycol ether product.

In one embodiment, the inventive process further comprises the step of (F) transferring the recycle phenolic stream to the first reactor or reaction zone. In one variation on this embodiment, the recycle phenolic stream is mixed with fresh phenolic compound and/or catalyst before it is transferred to the first reactor or reaction zone.

In another embodiment, the inventive process efficiently produces mono- and di-phenolic glycol ether products, e.g., di- and/or triethylene glycol phenyl ether, di- and/or tripropylene glycol phenyl ether, etc, over a broad range of mono-/di-product weight ratios and over a broad range of conditions without recycling the mono-product, e.g., ethylene or propylene glycol phenyl ether. This is achieved by adjusting the basicity of the reacting system either by adding or subtracting basic or acidic homogeneous catalyst such that a high (e.g., >30), low (e.g., <1) or middling mono/di weight ratio can be produced. Little or none basic homogeneous catalyst (the less basic the reacting system) favors a low mono-/di-product weight ratio, i.e., it produces relatively less mono-product and relatively more di- or higher product. The more basic homogeneous catalyst used (the more basic the reacting system), the higher the mono-/di-product weight ratio, i.e., the less di- or higher product is made relative to the mono-product.

In one embodiment, glycol impurity build up is reduced by removing water from the phenol recycle stream in a water removal column. The purity of the product is further enhanced by removing the product in the pasteurization section of the second distillation column to reduce phenol impurity and/or by feeding the catalyst into the phenol recycle stream before the stream enters the drying column and purging mono-ethylene glycol (MEG) and other light impurities containing phenol stream in the distillate of the second separation column.

The invention eliminates the need for catalyst neutralization and salt filtration and this, in turn, provides the option of recycling catalyst and reducing operating costs. Moreover, the high phenolic compound to oxide ratio that is used in this process provides a higher selectivity to the desired phenolic glycol ether, e.g., EPh and/or PPh, and this simplifies the purification process. The invention also eliminates the need for mono-product recycle in those instances in which a lower mono-/di-product weight ratio is desired.

BRIEF DESCRIPTION OF THE DRAWING

FIG. 1A is a flow diagram for the manufacture of propylene glycol phenyl ether employing a relatively small amount of basic homogeneous catalyst and favoring a relatively low mono-/di-product ratio.

DESCRIPTION OF THE PREFERRED EMBODIMENT

Figure 1B:
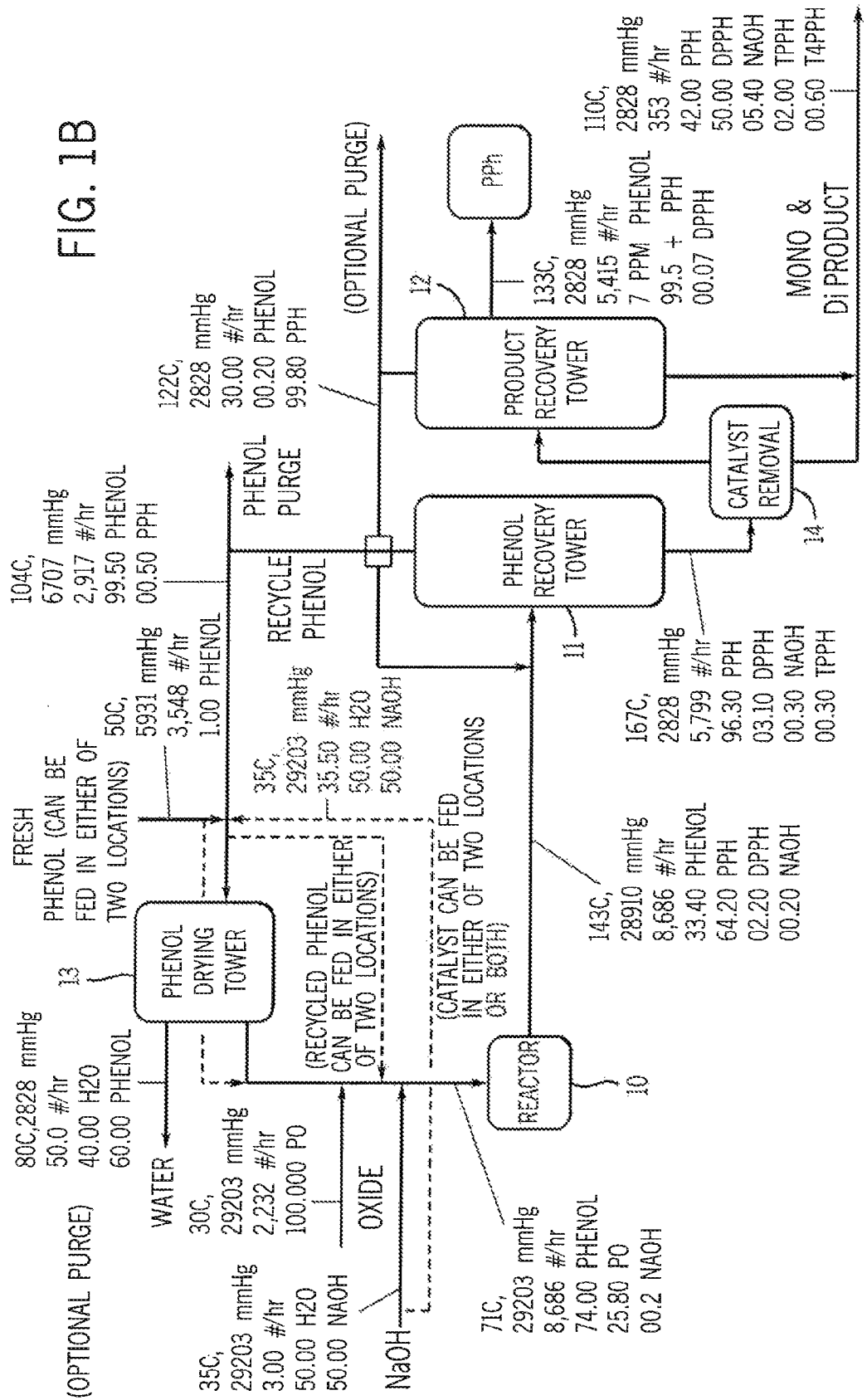
FIG. 1B is a flow diagram for the manufacture of propylene glycol phenyl ether employing a relatively large amount of basic homogeneous catalyst and favoring a relatively high mono-/di-product ratio with the option of using a catalyst removal or neutralization scheme.
Figure 2:
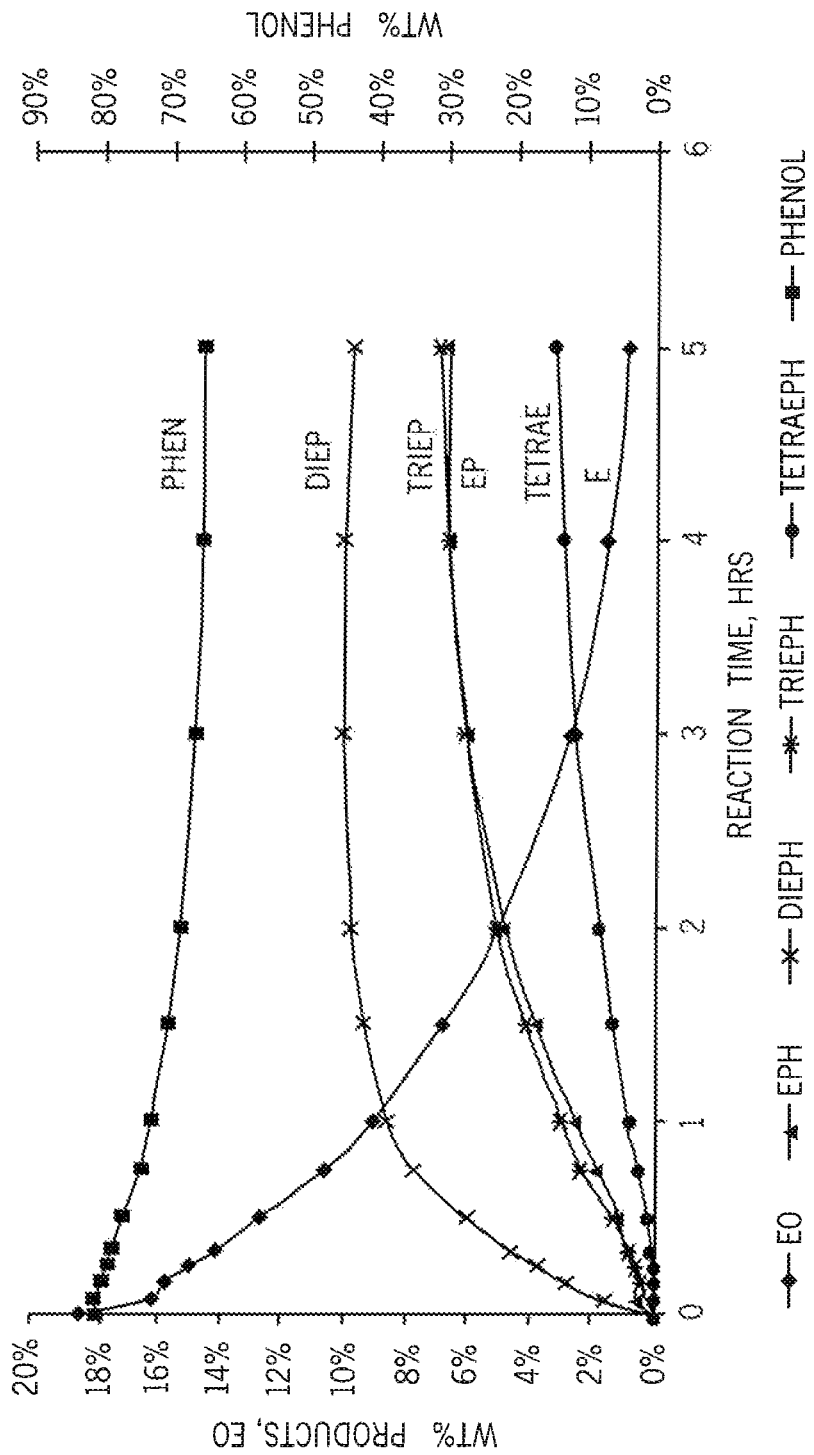
FIG. 2 is a graph reporting the reaction progress of the phenol, ethylene oxide and trifluoroacetic acid catalyst of Example 2.
Figure 3:
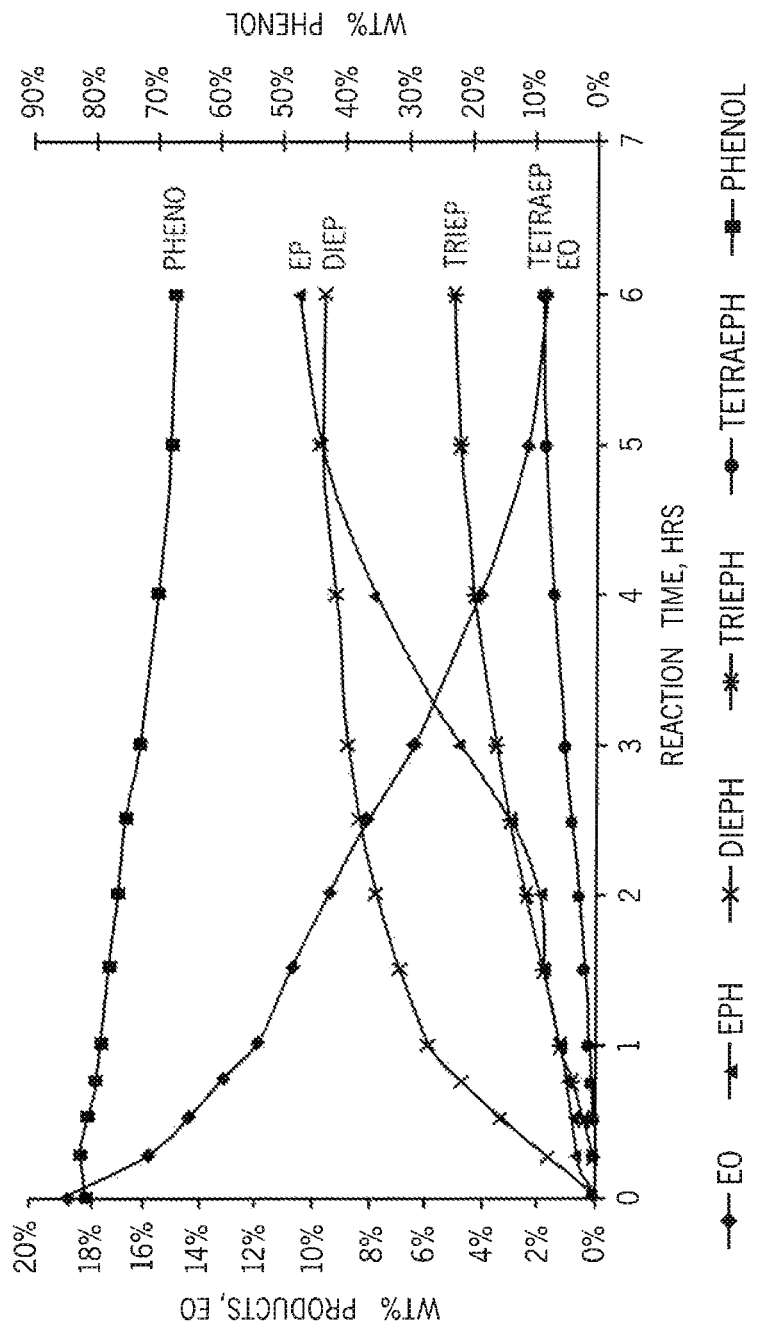
FIG. 3 is a graph reporting the reaction progress of the phenol and ethylene oxide without a catalyst of Example 3.
Figure 4:
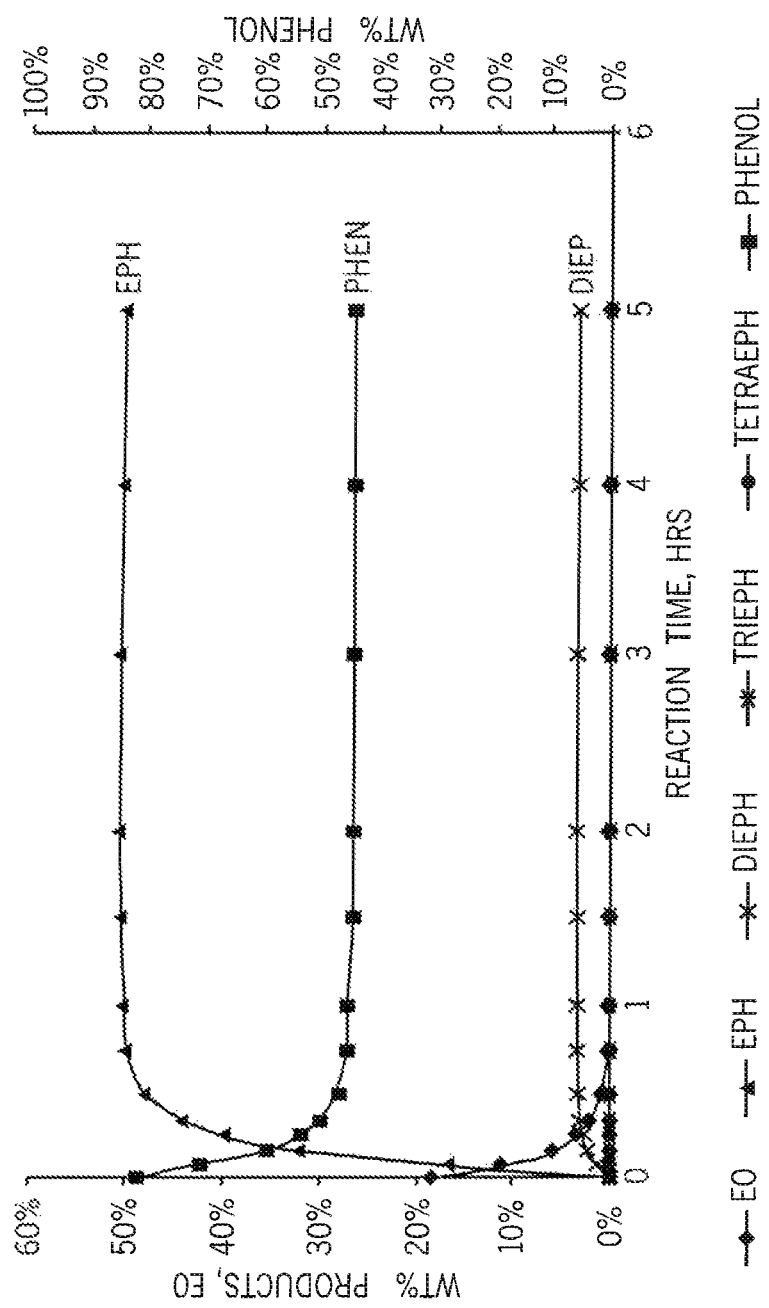
FIG. 4 is a graph reporting the reaction progress of the phenol, ethylene oxide and sodium hydroxide catalyst of Example 4.
Figure 5:
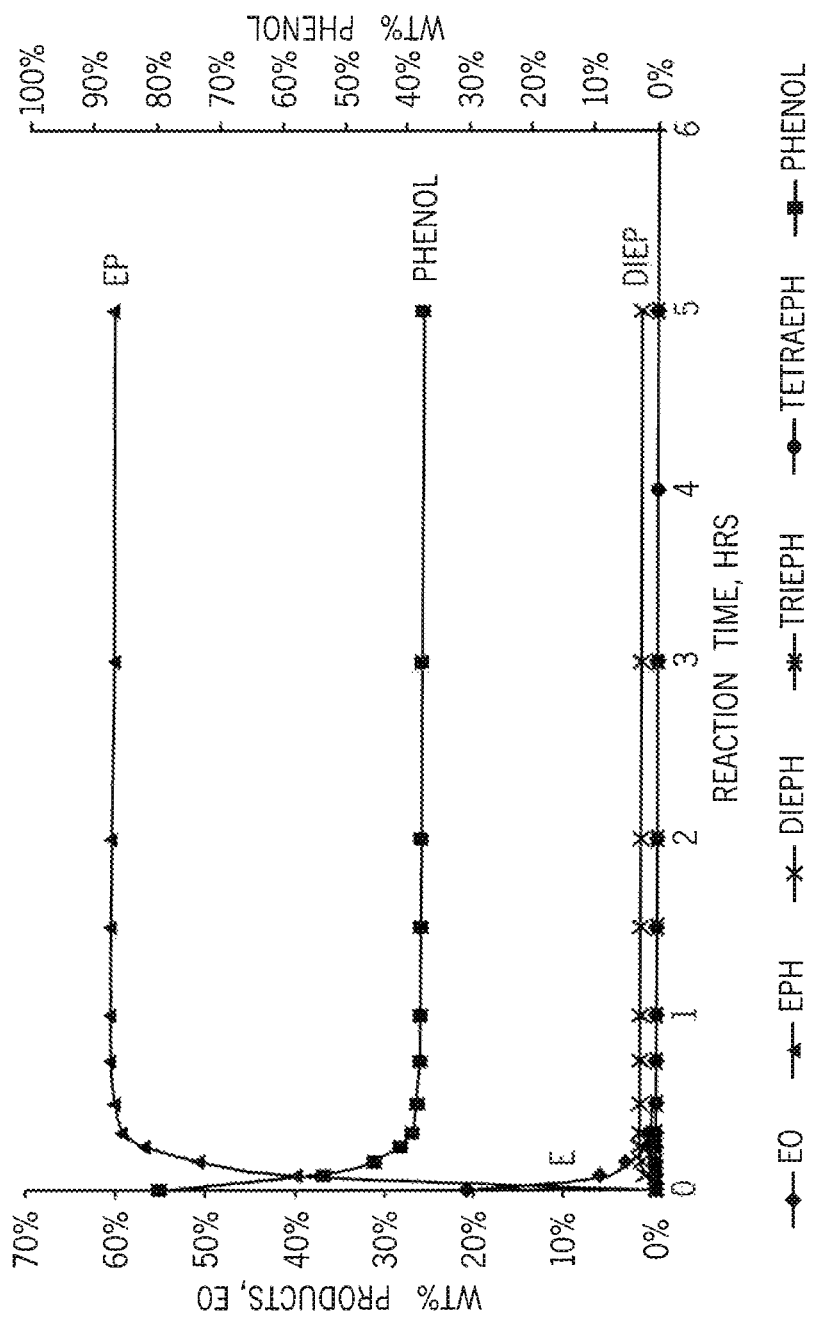
FIG. 5 is a graph reporting the reaction progress of the phenol, ethylene oxide and sodium hydroxide catalyst of Example 5.
Figure 6:
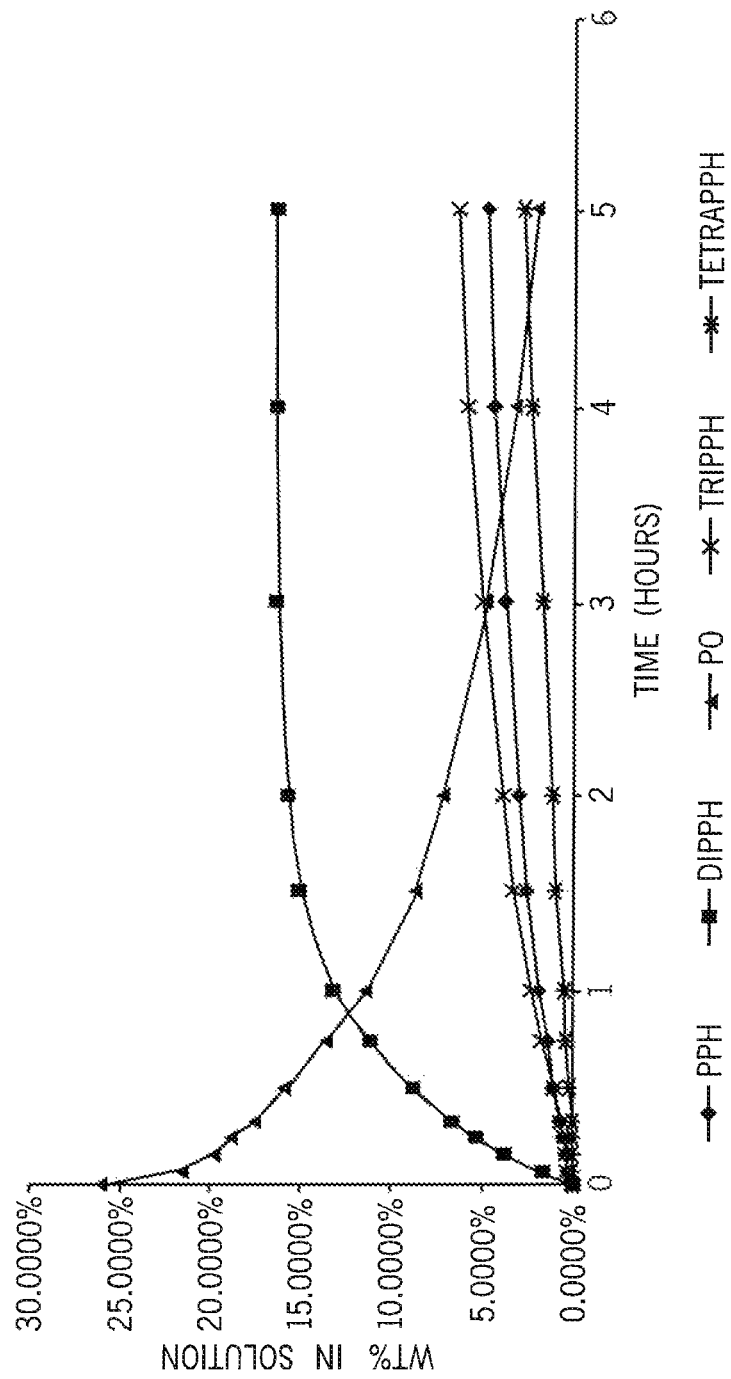
FIG. 6 is a graph reporting the reaction progress of the phenol and propylene oxide without a catalyst of Example 6.
Figure 7:
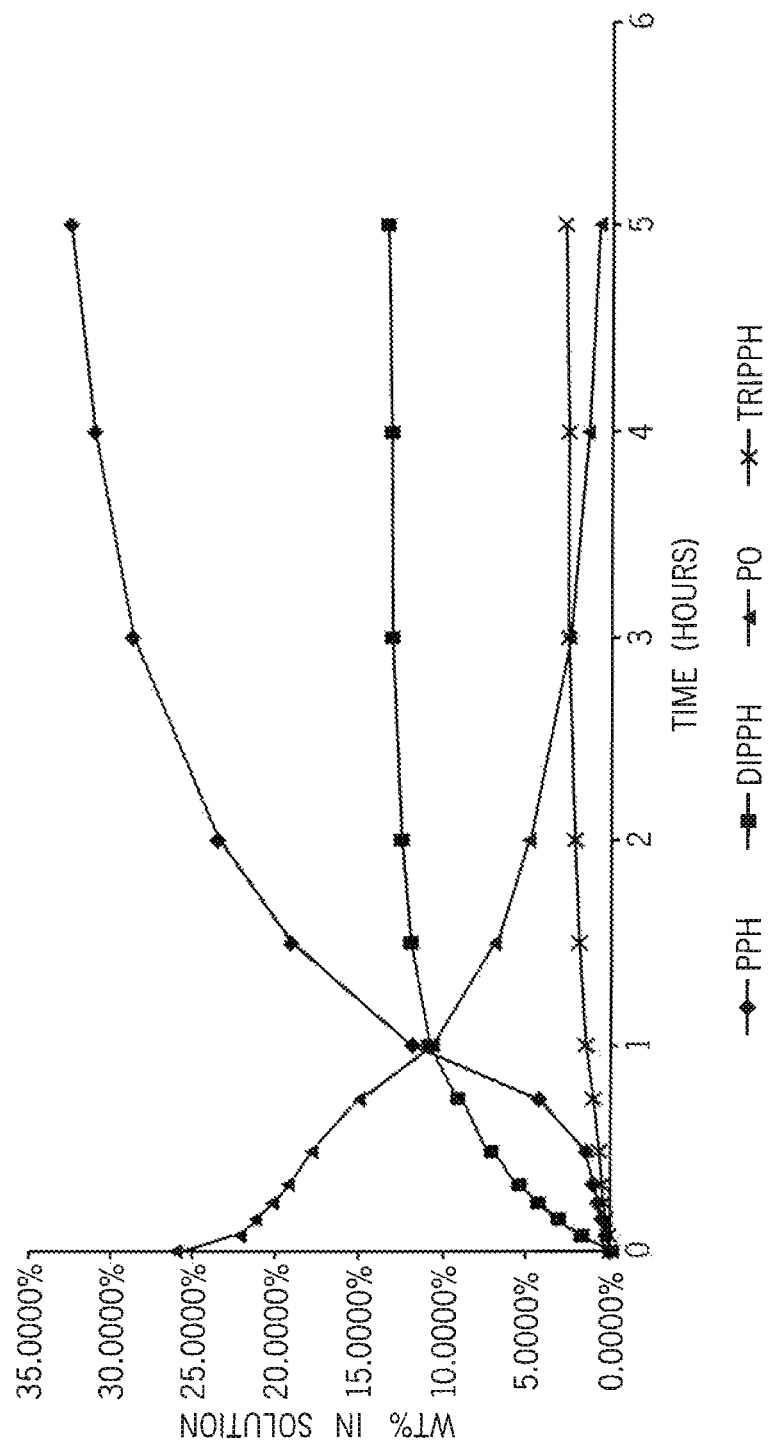
FIG. 7 is a graph reporting the reaction progress of the phenol, propylene oxide and aqueous sodium hydroxide catalyst of Example 7.
Figure 8:
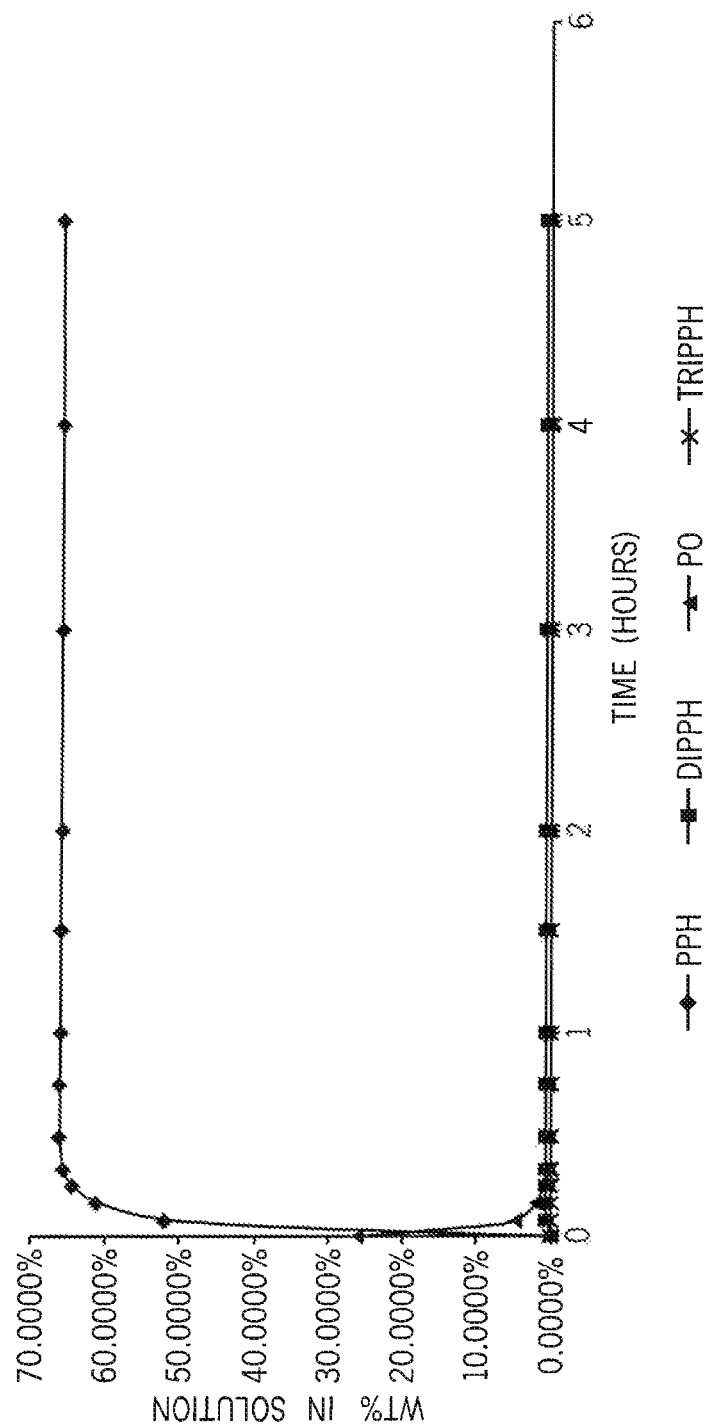
FIG. 8 is a graph reporting the reaction progress of the phenol, propylene oxide and aqueous sodium hydroxide catalyst of Example 8.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, melt index, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the relative amount of oxide to phenol, the relative amount of catalyst in the reaction mass, and various temperature and other process parameters.

"Catalytic amount" means the amount necessary to promote the reaction of a phenolic compound and an alkylene oxide under reactive conditions to form phenolic glycol ether at a detectable level, preferably at a commercially acceptable level. If a catalyst is used, then typically, the minimum amount of catalyst is at least 100 parts per million (ppm).

"Homogeneous catalyst" and like terms means a catalyst that is dispersed, preferably uniformly, through the phenolic compound or reaction mass as opposed to, for example, a catalyst bound to an ion exchange resin or a fixed-bed catalyst.

"Basic homogeneous catalyst" and like terms means a homogenous catalyst that in aqueous solution has a pH greater than 7.

"Acidic homogeneous catalyst" and like terms means a homogeneous catalyst that in aqueous solution has a pH of less than 7.

"Isothermal reactive conditions", "isothermal reactor", "isothermal reaction zone", "isothermal reaction" and like terms mean reactive conditions in which the temperature is held constant, or the temperature of the reactor or zone is held constant, or a chemical reaction proceeds to completion at one temperature, i.e., a change in temperature is not necessary for the reaction to continue to completion.

"Adiabatic reactive conditions", "adiabatic reactor", "adiabatic reaction zone", adiabatic reaction" and like terms mean reactive conditions, or a reactor or zone, or a reaction in which little, if any, loss or gain of heat from external sources occurs or is experienced.

"First intermediate phenolic glycol ether product" and like terms means the product that is produced from the reaction of a phenolic compound with an alkylene oxide in an isothermal reactor or reaction zone. This product includes not only phenolic glycol ether, but also catalyst, unreacted phenolic compound and alkylene oxide, water and byproducts.

"Second intermediate phenolic glycol ether product" and like terms means the product that is produced from the reaction of a phenolic compound with an alkylene oxide in an adiabatic reactor or reaction zone. This product includes all the components of the first intermediate phenolic glycol ether product but at different compositional ratios, e.g., it contains more phenolic glycol ether and less unreacted alkylene oxide and phenolic compound.

"Reaction mass", "reacting system" and like terms means the combination of materials necessary or ancillary to a reaction, typically under reactive conditions. Depending upon the moment in time in which the reaction mass is characterized, it will or can contain the reactants, catalyst, solvent, products, byproducts, impurities and the like. The typical reaction mass that forms a part of this invention after the reaction has begun will include unreacted alkylene oxide and phenolic compound, an alkali metal hydroxide, phenolic glycol ether, byproduct glycols and water.

"Nonaqueous process" and like terms means in the context of this invention that the reaction mass contains little, if any, water. In the process of this invention, the only water intentionally introduced into the reaction mass is that necessary to dissolve and assist in the dispersion of the catalyst. Any other water present is either a byproduct of the reaction chemistry or as an impurity associated with one of the reactants. The total amount of water in the second intermediate phenolic glycol ether product typically does not exceed 1 wt %, preferably does not exceed 0.5 wt % and more preferably does not exceed 500 ppm based on the weight of the second intermediate phenolic glycol ether product.

"Continuous process" and like terms means that the process is operated at a steady state, i.e., the reactants are fed to the reactor or reaction zone at a rate substantially in balance with the rate that product is removed from the reactor or reaction zone such that the reaction mass in the reactor or reaction zone is relatively constant in volume and composition. Continuous process does not include a batch or semi-batch process, the former characterized by a depletion of reactants and a growth of product over time, and the latter typically characterized by the unbalanced addition of reactant and removal of product over time.

Phenols, sometimes called phenolics, are a class of organic compounds consisting of a hydroxyl group (—OH) attached to an aromatic hydrocarbon group. The simplest of the class is phenol ($C_6H_5OH$). The phenolic compounds that can be used in the practice of this invention are typically monovalent and include phenol: phenols having a hydrocarbon substituent such as o-, m- or p-cresol, o-, m- or p-ethyiphenol, o-, m- or p-t-butylphenol, o-, m-, or p-octylphenol, 2,3-xylenol, 2,6-xylenol, 3,4-xylenol, 3-5-xylenol, 2,4-di-t-butylphenol; phenols having a substituent group such as an aromatic substituent or an aromatic ring e.g., o-, m- or p-phenylphenol, p-alpha-cumyl)phenol, and 4-phenoxyphenol; phenols having an aldehyde group such as o-, m- or p-hydroxybenzaldehyde; phenols having a substituent group with an ether linkage such as guaiacol and guaethol; phenols having a substituent group such as a hydroxyl group with a property inherent to alcohol (hereinafter, called as "alcoholic hydroxyl group") e.g., p-hydroxyphenethyl alcohol; phenols having a substituent group with an ester linkage such as p-hydroxy benzoic methyl, p-hydroxyphenylacetic acid methyl ester, and heptylparaben; and phenols having a halogen group such as 2,4,6-trichlorophenol. Among these, phenol and cresol are preferred. These phenols may be used alone or in any combination with one another.

The alkylene oxides (also known as epoxides) that can be used in the practice of this invention include ethylene oxide, propylene oxide, isobutylene oxide, 1,2-butylene oxide, 2,3-butylene oxide, and pentylene oxide; aromatic alkylene oxides such as stylene oxide; and cyclohexane oxide. These alkylene oxides may be used alone or in any combination with one another. Among the alkylene oxide compounds, preferred are aliphatic alkylene oxides having 2 to 4 carbon atoms such as ethylene oxide, propylene oxide, isobutylene oxide, and 2,3-butylene oxide. Although the alkylene oxide is typically added as a liquid, it can be added as a gas.

While the catalyst used in the practice of this invention can be any appropriate acid or base, e.g., a Lewis acid or base, preferably the catalyst is a base. Alkaline materials effective for catalyst generation include alkali metals, alkali hydroxides and carbonates, alkaline earth metal hydroxides, tetraalkyl ammonium hydroxide and organic bases (e.g., pyridine, trimethyl amine and imidazole). The preferred catalysts are sodium hydroxide and potassium hydroxide. The catalyst, can be added neat, usually dissolved in a small amount of water, or formed in situ. The catalyst is used in a homogeneous manner, i.e., it is dispersed, preferably uniformly, through the reaction mass. Typically, the catalyst is mixed with the phenolic compound before the phenolic compound is mixed with the alkylene oxide.

In the process of this Invention, the phenolic compound, alkylene oxide and catalyst are continuously added in any conventional manner to an isothermal reactor or the isothermal zone of a multizone reactor. The phenolic compound is added in excess relative to the alkylene oxide and as noted above, the catalyst is often pre-mixed with the phenolic compound, e.g., as part of a phenolic recycle stream, before the alkylene oxide is mixed with the phenolic compound, etc. The size of the excess amount of phenolic compound can and will vary with the desired operation of the process and product mix. Typically the more phenol present, the faster the reaction proceeds and the fewer by-products are made. However, the more phenol present also means the more energy required to operate the distillation towers or other separation equipment needed to recover and recycle the unreacted phenol from the product. The phenolic compound is typically present in a stoichiometric molar excess ranging from as little as 0.5% to as much as 100% or even 200%.

The phenolic compound, alkylene oxide and catalyst are contacted with one another in the isothermal reactor or zone under isothermal reactive conditions. These conditions include a temperature between ambient (e.g., 23° C.) and 200° C., preferably between 100° C. and 180° C. and more preferably between 120° C. and 170° C., and a pressure between 8,000 and 50,000 millimeters of mercury at 0° C. (mmHg, or between 1.067 and 6.667 megaPascal (mPa)), preferably between 20,000 and 40,000 mmHg (2.067 and 5.333 mPa) and more preferably between 25,000 and 35,000 mmHg (3.333 and 4.666 mPa). The reaction mass in the isothermal reactor or zone is essentially free of water except for that used to dissolve the catalyst or that formed as a byproduct or introduced as an impurity, and it is subject to agitation by any conventional means, e.g., stirring, turbulent flow, etc. The reaction mass is resident in the isothermal reactor or zone until a majority of the alkylene oxide is converted thus forming a first intermediate phenolic glycol ether product, and then this product is transferred by any means to an adiabatic reactor or zone in which essentially all of the remaining alkylene oxide is converted to form the second intermediate phenolic glycol ether product. The isothermal and adiabatic reaction zones can be reactors that are separate and distinct from one another and simply connected in series, or they can be zones within a single reactor structure. For example, the isothermal reactor can be a coiled reactor consisting of multiple spiral parallel coils of varying number (e.g., 2-4 coils) within a boiling bath all contained in a metal shell. The heat of reaction is removed via boiling water on the shell side of the coils while the reactive process occurs within the coils themselves. The adiabatic section can be simply volume designed (whether it is insulated piping or an insulted process vessel) to provide sufficient residence for complete oxide conversion. The temperature of the first reactor zone may be different, and is typically lower, than the temperature of the second reactor zone. This temperature difference is typically between 0 and 40, more typically between 0 and 20 and even more typically between 0 and 10° C. Other than this temperature difference, the adiabatic reactive conditions of the adiabatic reactor or zone are essentially the same as the isothermal reactive conditions of the isothermal reactor or zone. The temperature of the first intermediate phenolic glycol ether product typically may be adjusted to the temperature of the adiabatic reactor or zone by passing through one or more heat exchangers as it moves from the isothermal reactor or zone to the adiabatic reactor or zone.

Once the conversion of the alkylene oxide in the adiabatic reactor or reaction zone is complete, the second intermediate phenolic glycol ether product is discharged and subjected to a purification operation. Since unreacted phenolic compound is present in a large excess, its recovery and recycle are important to the economics of the overall process. Accordingly, the second intermediate phenolic glycol ether product is typically transferred to a separation station or zone, e.g., a first distillation column, in which the unreacted phenolic compound, catalyst and water are recovered and the remainder of the second intermediate phenolic glycol ether product is transferred to one or more additional distillation columns in which the phenolic glycol ether is recovered in high purity, typically greater than 95, preferably greater than 99 and more preferably greater than 99.5, wt % pure. In the second column (and additional columns if used), the purified phenolic glycol ether is recovered as a side-draw stream, and the overhead stream containing the remainder of the stream is returned to the first column to recover additional unreacted phenolic compound not recovered during the first pass.

The recovered phenolic compound and residual water stream from the first distillation column is then typically transferred to a drying station at which it is subjected to a drying operation. An example of a drying station is a multistage distillation column in which water (the lighter component) is physically separated from phenol (the heavier component) by adjusting the temperature and pressure profile in the column. Fresh phenol and/or catalyst can be added before the drying column so as to remove any water present in these materials. The resulting phenol and catalyst mixture is removed and returned to the reactor system. Other drying methods that can be used include mole-sieve, desiccant and membrane.

The process of this invention is particularly useful for the production of EPh and/or PPh from phenol, ethylene and/or propylene oxide, and sodium or potassium hydroxide catalyst. By use of a large excess of phenol, minimal, if any, water and a homogeneous catalyst, EPh and PPh are selectively made with a minimum production of glycol byproducts.

One hallmark of this embodiment of the present invention is the production in a continuous, essentially nonaqueous process of high purity phenolic glycol ether. In one embodiment, additional hallmarks include use of an excess of phenolic compound and a homogeneous catalyst, and conducting the process first in an isothermal reactor or reaction zone and then in an adiabatic reactor or reaction zone. In another embodiment, additional hallmarks are the recovery, drying and recycle of unreacted phenolic compound.

In the embodiment in which the mono-/di-product weight ratio is affected by adjusting the basicity of the reacting system by adding or subtracting basic or acidic homogeneous catalyst, the amount of catalyst added will vary with the degree to which the mono-/di-product weight ratio is to be adjusted. The more basic homogeneous catalyst added, the less di product formed and thus the higher the weight ratio. Typically, the amount of catalyst ranges from none to 4,000 ppm. As the amount of basic homogeneous catalyst approaches 4,000 ppm, the more basic is the reacting system, the more mono-product and the less di-product are produced, and thus the higher the mono-/di-product weight ratio obtained. As the amount of catalyst approaches 0, the less basic is the reacting system, the less mono-product and the more di-product are produced, and thus the lower mono/di weight ratio obtained. The exact mono-/di-product weight ratio achieved will depend upon a number of different factors in addition to the amount of basic catalyst in the reaction mass, e.g., the composition of alkylene oxide and phenol and their amounts relative to one another, the temperature and pressure of the reactor and the residence time of the reaction mass in the reactor, whether isothermal or adiabatic reaction conditions, or a combination of the two, are used, and the like.

SPECIFIC EMBODIMENT

In the following examples, all amounts are approximate. Minor components, e.g., glycols, acetones, acetols, alpha-methyl styrene, aldehydes and the like are not reported because of their low concentration, and their respective amounts vary with the purge rates. Purges are optional as are certain recycle loops and reagent entry points. Amounts are in weight percent unless otherwise noted, and the catalyst concentration can range from none to 4000 parts per million (ppm), or significantly more than 4000 ppm if a catalyst removal or neutralization scheme is employed.

Example 1A

FIG. 1A illustrates an example of preparing propylene glycol phenyl ether (PPh) by an embodiment of this invention in which a small amount (0.05 wt %, relative to Example 1B) of basic homogeneous catalyst (sodium hydroxide) is used. This embodiment favors the production of less mono-product (i.e., propylene glycol phenyl ether) and more di-product (dipropylene glycol phenyl ether), and thus a low mono-/di-product weight ratio (58:5 or 11.6) relative to Example 1B.

Propylene, oxide (26 wt %), phenol (74 wt %) and sodium hydroxide catalyst (500 ppm or 0.05 wt %) are fed to a first zone of reactor 10 in which they are contacted with one another under isothermal conditions (150° C. and 29,200 mmHg (3.89 mPa) at the inlet to the first zone) to form a first intermediate phenolic glycol ether product. This first product is then transferred along with unreacted starting materials and any by-products to a second zone of reactor 10 in which all are subjected to adiabatic reactive conditions (150-171° C. and 29,082 mmHg (3.877 mPa) at the inlet to the second zone) to form a second intermediate product. This product leaves reactor 10 at 171° C. and 28,853 mmHg (3.847 mPa) and a rate of about 8,700 pounds per hour. This second product comprises, among other components, phenol (36 wt %), propylene glycol phenyl ether (58 wt %), dipropylene glycol phenyl ether (5 wt %) and 0.05 wt % sodium hydroxide catalyst.

The second product is fed to phenol recovery distillation tower 11, optionally first mixed with the overhead stream from product recovery tower 12. Phenol is taken overhead from tower 11, mixed with fresh phenol and fed to phenol drying tower 13 in which water is removed along with minor amounts of other impurities. From drying tower 13, dehydrated phenol is mixed with fresh propylene oxide and sodium hydroxide catalyst, and looped back to reactor 10.

The second product minus the recovered phenol is taken as a bottom stream from recovery tower 11 and fed to product recovery tower 12. The second product exiting phenol recovery tower 11 comprises 90 wt % PPh, 8 wt % dipropylene glycol phenyl ether and minor amounts of tri- and tetrapropylene glycol phenyl ether and catalyst. In product recovery tower 12, an overhead stream is recycled back for mixing with the second intermediate product prior to this second product being fed to phenol recovery tower 11. Mono- (5.6 wt %), di- (77.7 wt %), tri- (11.6 wt %) and minor amounts of tetra- and quinto-propylene glycol phenyl ether is recovered as a bottoms stream, and finished product (greater than 99.5 wt % PPh) is recovered as a side stream.

Example 1B

FIG. 1B illustrates an example of preparing propylene glycol phenyl ether (PPh) by an embodiment of this invention in which a large amount (0.2 wt %, relative to Example 1A) of basic homogeneous catalyst (sodium hydroxide) is used. This embodiment favors the production of more mono-product (i.e., propylene glycol phenyl ether) and less di-product (dipropylene glycol phenyl ether), and thus a high mono-/di-product weight ratio (64.2:2.2 or 29.2) relative to Example 1A.

Propylene oxide (25.8 wt %), phenol (74 wt %) and sodium hydroxide catalyst (0.2 wt %) are fed to a first zone of reactor 10 in which they are contacted with one another under the isothermal conditions as reported in Example 1A to form a first intermediate phenolic glycol ether product. This first product is then transferred along with unreacted starting materials and any by-products to a second zone of reactor 10 in which all are subjected to the adiabatic reactive conditions as also reported in Example 1A to form a second intermediate product. This product leaves reactor 10 under essentially the same conditions are reported in Example 1A. This second product comprises, among other components, phenol (33.4 wt %), propylene glycol phenyl ether (64.2 wt %), dipropylene glycol phenyl ether (2.2 wt. %) and 0.2 wt % sodium hydroxide catalyst.

The second product is fed to phenol recovery distillation tower 11, optionally first mixed with the overhead stream from product recovery tower 12. Phenol is taken overhead from tower 11, mixed with fresh phenol and fed to phenol drying tower 13 in which water is removed along with minor amounts of other impurities, from drying tower 13, dehydrated phenol is mixed with fresh propylene oxide and sodium hydroxide catalyst, and looped back to reactor 10.

The second product minus the recovered phenol is taken as a bottom stream from recovery tower 11 but due to its relatively high catalyst content, it is passed through catalyst removal station 14 before it is fed to product recovery tower 12. In station 14 the catalyst can be either neutralized, e.g., by the addition of an acid such as phosphoric acid, or removed by any conventional procedure such as evaporation, e.g., boiling tube or rolled or falling film.

The second product exiting phenol recovery tower 11 comprises 96.3 wt % PPh, 3.1 wt % dipropylene glycol phenyl ether and minor amounts of tri- and tetrapropylene glycol phenyl ether and catalyst. In product recovery tower 12, an overhead stream is recycled back for mixing with the second intermediate product prior to this second product being fed to phenol recovery tower 11. Mono- (42 wt %), di- (50 wt %), tri- (2 wt %) and minor amounts of tetrapropylene glycol phenyl ether is recovered as a bottoms stream, and finished product (greater than 99.5 wt % PPh) is recovered as a side stream.

Examples 2-8

All of the following examples are conducted in a two-liter Parr reactor. In each example, the reactor is charged with about 400 grams (g) of phenol, optionally a catalyst, purged with nitrogen and then warmed to the reaction temperature. The oxide is then charged to the reactor over 12-42 seconds, and the reaction allowed to proceed for live hours. Samples are periodically removed and analyzed by gas chromatographic (GC) analysis. The progress of the reaction is reported in the figure that accompanies the example.

TABLE 1

Reactants and Reaction Temperature

| Ex. | Oxide | Oxide (g) | Catalyst | Cat (g) | R.T.[1] (° C.) |
|---|---|---|---|---|---|
| 2 | EO[2] | 90.6 | TFAA[4] | 2.2 | 160 |
| 3 | EO | 90 | None | — | 140 |
| 4 | EO | 91 | s-NaOH[5] | 0.3 | 160 |
| 5 | EO | 104.3 | aq-NaOH[6] | 2.46 | 140 |
| 6 | PO[3] | 140.4 | None | — | 170 |
| 7 | PO | 140.3 | aq-NaOH | 0.13 | 160 |
| 8 | PO | 141.7 | aq-NaOH | 4.68 | 160 |

[1]R.T. = Reaction Temperature
[2]EO = Ethylene Oxide
[3]PO = Propylene Oxide
[4]TFAA = Trifluoroacetic Acid
[5]s-NaOH = Solid Sodium Hydroxide
[6]aq-NaOH = 50% Aqueous Sodium Hydroxide

TABLE 2

Product Mix

| Ex. | Phenol (wt %) | Mono-Product[1] (wt %) | Di-Product[2] (wt %) | Tri-Product[3] (wt %) | Mono-/Di-Product Wt. Ratio |
|---|---|---|---|---|---|
| 2 | 65.8 | 6.8 | 9.8 | 7 | 0.69 |
| 3 | 67.2 | 10.5 | 9.6 | 5.1 | 1.09 |
| 4 | 44.9 | 50.4 | 3.5 | 0.3 | 14.4 |
| 5 | 37.2 | 60.7 | 1.5 | 0.1 | 40.47 |
| 6 | 59.4 | 4.9 | 16.7 | 6.6 | 0.29 |
| 7 | 45.6 | 32.9 | 13.6 | 2.8 | 2.42 |
| 8 | 32.3 | 66.3 | 0.9 | 0.01 | 73.67 |

[1]Mono-Product - Ethylene Glycol Phenyl Ether for Examples 2-5, and Propylene Glycol Phenyl Ether for Examples 6-8.
[2]Di-Product - Di-Ethylene Glycol Phenyl Ether for Examples 2-5, and Di-Propylene Glycol Phenyl Ether for Examples 6-8.
[3]Tri-Product - Tri-Ethylene Glycol Phenyl Ether for Examples 2-5, and Tri-Propylene Glycol Phenyl Ether for Examples 6-8.

Example 2 reports a product mix with a relatively low mono-/di-product ratio formed under predominately acidic conditions. The rate of DiEPh formation is second order in EO concentration. Example 3 reports that a near 1:1 mono-/di-product weight ratio is obtained by running the reaction without catalyst. Example 4 shows that predominantly EPh is generated under basic conditions, while Example 5 shows that a higher mono-/di-product weight ratio is obtained with a larger charge of base catalyst. Examples 6-8 show that the same relationships hold for the reaction of phenol with propylene oxide to make PPh and dipropylene glycol phenyl ether (DiPPh). The progress of the reactions of Examples 2-8 are reported in FIGS. 2-8, respectively.

Although the invention has been described in considerable detail by the preceding specification, this detail is for the purpose of illustration and is not to be construed as a limitation upon the following appended claims. All U.S. patents, allowed U.S. patent applications and U.S. Patent Application Publications are incorporated herein by reference.

What is claimed is:

1. A continuous, nonaqueous process for producing phenolic glycol ether, the process comprising the steps of (A) contacting under isothermal reactive conditions in a first reactor or reaction zone an alkylene oxide with (i) a stoichiometric molar excess of a phenolic compound, and (ii) a catalytic amount of a base homogeneously dispersed throughout the phenolic compound, to form a first intermediate phenolic glycol ether product, (B) transferring the first intermediate phenolic glycol ether product to a second reactor or reaction zone, and (C) subjecting the first intermediate phenolic glycol ether product to adiabatic reactive conditions at an exit temperature greater than that of step (A) in the second reactor or reaction zone to form a second intermediate phenolic glycol ether product comprising phenolic glycol ether, unreacted phenolic compound, catalyst, water and byproduct glycols, wherein the phenolic glycol ether comprises mono-alkyl phenolic glycol ether and di-alkyl glycol phenolic ether and the ratio of mono-alkyl phenolic glycol ether to di-alkyl glycol phenolic ether is determined by the amount of the base.

2. The process of claim 1 further comprising the step of (D) transferring the second intermediate phenolic glycol ether product from the second reactor or reaction zone to a separation station or zone at which unreacted phenolic compound and water are separated and recovered from the second intermediate phenolic glycol ether product to form a recovered phenolic stream comprising unreacted phenolic compound and water, and a purified second intermediate phenolic glycol ether product stream.

3. The process of claim 2 further comprising the step of (E) optionally adding fresh catalyst or phenol to the recovered phenolic stream, and transferring the stream to a drying station at which water is removed from the stream to form a recycle phenolic stream comprising unreacted phenolic compound and, optionally, fresh phenol or catalyst.

4. The process of claim 3 further comprising the step of (F) transferring the recycle phenolic stream to the first reactor or reaction zone.

5. The process of claim 3 in which the recycle phenolic stream is mixed with fresh phenolic compound and/or catalyst before the recycle phenolic stream is transferred to the first reactor or reaction zone.

6. The process of claim 1 in which the phenolic compound is phenol, the alkylene oxide is at least one of ethylene oxide and propylene oxide, and the catalyst is at least one of sodium hydroxide and potassium oxide.

7. The process of claim 2 in which at least one of the following is performed: (a) the unreacted phenolic compound and water are separated and recovered from the second intermediate phenolic glycol ether product by distillation, or (b) water is removed from the phenolic stream by distillation, or (c) the purified second intermediate phenolic glycol ether product stream is transferred to a catalyst removal station in which catalyst is removed from the stream and neutralized by the addition of an acid.

8. A method for adjusting the mono-/di-alkyl phenolic glycol ether product weight ratio of a product comprising mono-alkyl phenolic glycol ether and di-alkyl glycol phenolic ether, the product produced by a process comprising the step of contacting under nonaqueous reactive conditions at least one phenol, at least one alkylene oxide and at least one basic homogeneous catalyst, the method comprising the step of increasing the concentration of the catalyst to increase the mono-/di-product weight ratio or decreasing the concentration of the catalyst to decrease the mono-/di-product weight ratio.

9. The method of claim 8 in which the catalyst is a Lewis base, and the basicity of the reaction mass is adjusted by adding more Lewis base.

* * * * *